United States Patent [19]
Chen

[11] Patent Number: 5,492,754
[45] Date of Patent: Feb. 20, 1996

[54] ABSORBENT COMPOSITION INCLUDING A MAGNETICALLY-RESPONSIVE MATERIAL

[75] Inventor: Franklin M. C. Chen, Appleton, Wis.

[73] Assignee: Kimberly-Clark Corporation, Neenah, Wis.

[21] Appl. No.: 168,806

[22] Filed: Dec. 15, 1993

[51] Int. Cl.$^6$ .................. C04B 35/64; G01N 31/00
[52] U.S. Cl. .................. 428/284; 148/100; 148/103; 148/105; 148/108; 252/62.53; 252/315.3; 252/408.1; 428/692; 428/913; 604/358
[58] Field of Search .................. 252/62.51, 62.54, 252/315.3, 62.53, 408.1; 148/100, 103, 105, 108; 604/358; 436/149; 428/284, 692, 913

[56] References Cited

U.S. PATENT DOCUMENTS

| | | | |
|---|---|---|---|
| 3,618,619 | 11/1971 | Kiefer | 131/266 |
| 3,997,484 | 12/1976 | Weaver et al. | 260/17.4 GC |
| 4,335,094 | 6/1982 | Mosbach | 424/1 |
| 4,364,377 | 12/1982 | Smith | 128/1.5 |
| 4,375,407 | 3/1983 | Kronick | 209/8 |
| 4,474,866 | 10/1984 | Ziolo | 430/106.6 |
| 5,143,583 | 9/1992 | Marchessault et al. | 162/138 |
| 5,298,179 | 3/1994 | Ukita et al. | 252/62.54 |

FOREIGN PATENT DOCUMENTS 2155952  6/1990  Japan.

OTHER PUBLICATIONS

Derwent Abstract of JP 5605574.
Derwent Abstract of JP 63075080.
Derwent Abstract of JP 1004331 A.
Derwent Abstract of JP 1095174 A.
Derwent Abstract of JP 4093381 A.
Derwent Abstract of JP 61248503.
Derwent Abstract of SU 1745328–A.

*Primary Examiner*—James J. Bell
*Attorney, Agent, or Firm*—John R. Schenian

[57] ABSTRACT

Disclosed is an absorbent composition including a hydrogel-forming polymeric material and a magnetically-responsive material; disposable absorbent products, including the absorbent composition, intended for the absorption of body fluids; and a method for incorporating the absorbent composition into disposable absorbent products.

18 Claims, 6 Drawing Sheets

ABSORBENT COMPOSITION INCLUDING A MAGNETICALLY-RESPONSIVE MATERIAL

BACKGROUND OF THE INVENTION

1. Field of the Invention

The present invention relates to an absorbent composition including a hydrogel-forming polymeric material and a magnetically-responsive material; disposable absorbent products, including the absorbent composition, intended for the absorption of body fluids; and a method for incorporating the absorbent composition into disposable absorbent products.

2. Description of the Related Art

The use of hydrogel-forming polymeric materials, commonly known as superabsorbents, in disposable absorbent personal care products is known. Such absorbent materials are generally employed in absorbent products such as diapers, training pants, adult incontinence products, and feminine care products in order to increase the absorbent capacity of such products while reducing their overall bulk. Such absorbent materials are generally present in absorbent products in a fibrous matrix, such as a matrix of wood pulp fluff. A matrix of wood pulp fluff generally has an absorbent capacity of about 6 grams of liquid per gram of fluff. The absorbent materials described above generally have an absorbent capacity of at least about 10, preferably of about 20, and often of up to 100 times their weight in water. Clearly, incorporation of such absorbent materials in personal care products can reduce the overall bulk while increasing the absorbent capacity of such products.

A wide variety of materials have been described for use as hydrogel-forming polymeric materials in such personal care products. Such materials include natural-based materials such as agar, pectin, gums, carboxyalkyl starch, and carboxyalkyl cellulose, as well as synthetic materials such as polyacrylates, polyacrylamides, and hydrolyzed polyacrylonitrile.

Various methods of incorporating a hydrogel-forming polymeric material into a personal care product are known. One such method includes using a vacuum process to prepare a layered absorbent structure comprising a tissue web base and a hydrogel-forming polymeric material layer ideally located between two wood pulp fluff layers. A tissue web base moves over a vacuum drum former which attracts the desired wood pulp fluff and hydrogel-forming polymeric material from a forming chamber. In practice, however, turbulent air flow in the forming chamber typically results in an absorbent structure without a clear-cut layered structure wherein the hydrogel-forming polymeric material is somewhat randomly distributed within the wood pulp fluff layers.

Another vacuum process may be used to form an absorbent structure wherein the hydrogel-forming polymeric material is distributed within a porous tissue web base. Again, a tissue web base moves over a vacuum drum former which attracts the desired hydrogel-forming polymeric material from a forming chamber. The porosity of the tissue web base permits the absorbent material to become distributed within the tissue web base. However, the pore size distribution of the tissue web base typically overlaps the particle size distribution of the hydrogel-forming polymeric material particles such that an amount of the hydrogel-forming polymeric material will not be distributed within the tissue web base and will generally result in air borne hydrogel-forming polymeric material particles as the absorbent structure is further processed.

Another method of incorporating a hydrogel-forming polymeric material into a personal care product includes using a gravimetric process wherein the hydrogel-forming polymeric material is gravimetrically applied to a moving tissue web base with adhesive lines applied on the surface of the tissue web base. Typically, an amount of the hydrogel-forming polymeric material does not contact the adhesive lines so that such hydrogel-forming polymeric material is not adhered onto the t issue web base.

Such known processes for incorporating a hydrogel-forming polymeric material into a disposable absorbent product typically result in placement of an amount of the hydrogel-forming polymeric material in undesired locations within the personal care product. Such an inefficient placement of the hydrogel-forming polymeric material generally results in the use of more of the hydrogel-forming polymeric material than would ideally be needed, thereby increasing the costs of manufacturing the personal care product. Additionally, the presence of the hydrogel-forming polymeric material in undesired locations within the personal care product may negatively affect the designed performance of the personal care product. Furthermore, the inefficient placement of the hydrogel-forming polymeric material often results in airborne hydrogel-forming polymeric material particles which can create health and safety problems.

SUMMARY OF THE INVENTION

Figure 1:
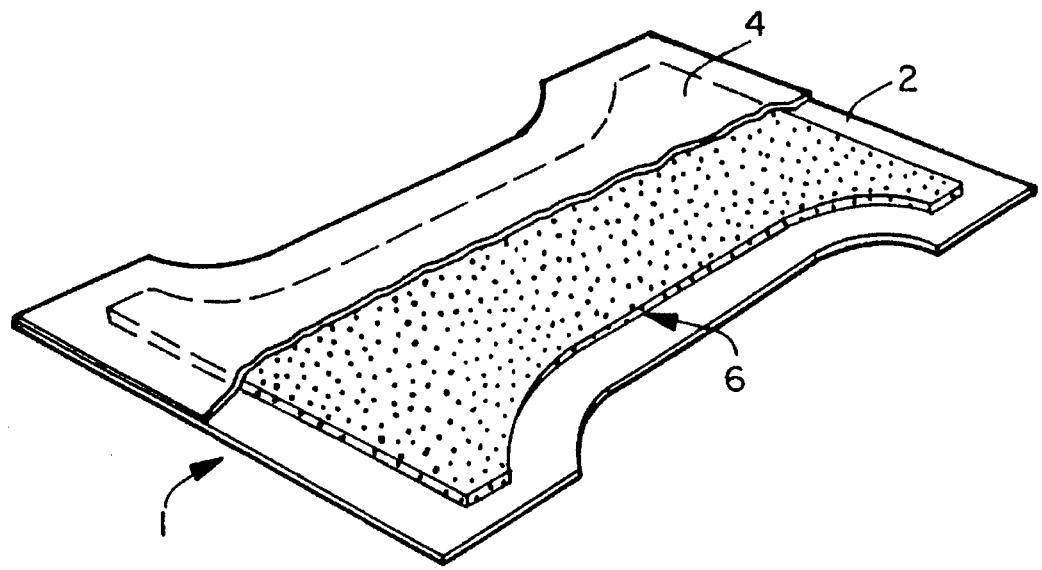
FIG. 1 represents a disposable diaper according to the present invention.

The present invention concerns an efficient and effective manner for incorporating a hydrogel-forming polymeric material into a personal care product wherein the placement of the hydrogel-forming polymeric material may be substantially controlled.

One aspect of the present invention concerns an absorbent composition comprising a hydrogel-forming polymeric material and a magnetically-responsive material.

One embodiment of such an absorbent composition comprises a hydrogel-forming polymeric material and a magnetically-responsive material selected from the group consisting of ferrimagnetic materials and superparamagnetic materials wherein the magnetically-responsive material is present in the absorbent composition in an amount effective to result in the absorbent composition being magnetically responsive when in a magnetic field, yet the absorbent composition remains substantially unmagnetized when a magnetic field is absent.

In another aspect, the present invention concerns a disposable absorbent product for the absorption of liquids such as body liquids.

One embodiment of such a disposable absorbent product comprises a liquid-permeable topsheet, a backsheet, and an absorbent structure positioned between the topsheet and the backsheet, wherein the absorbent structure comprises an absorbent composition comprising a hydrogel-forming polymeric material and a magnetically-responsive material.

In another aspect, the present invention concerns a process for incorporating an absorbent composition comprising a hydrogel-forming polymeric material and a magnetically-responsive material into a personal care product.

One embodiment of such a process comprises using a magnetic field to contact a composition comprising a hydrogel-forming polymeric material and a magnetically-responsive material with a disposable absorbent structure.

DETAIL DESCRIPTION OF THE PREFERRED EMBODIMENTS

One aspect of the present invention concerns an absorbent composition comprising a hydrogel-forming polymeric material and a magnetically-responsive material.

As used herein, "hydrogel-forming polymeric material" is meant to refer to a high-absorbency material commonly referred to as a superabsorbent material. Such high-absorbency materials are generally capable of absorbing an amount of a liquid, such as water, synthetic urine, a 0.9 weight percent aqueous saline solution, or bodily fluids, such as menses, urine, or blood, at least about 10, suitably about 20, and up to about 100 times the weight of the superabsorbent material at the conditions under which the superabsorbent material is being used. Typical conditions include, for example, a temperature of between about 0° C. to about 100° C. and suitably ambient conditions, such as about 23° C. and about 30 to about 60 percent relative humidity. Upon absorption of the liquid, the superabsorbent material typically swells and forms a hydrogel.

The superabsorbent material may be formed from an organic hydrogel material which may include natural materials, such as agar, pectin, and guar gum, as well as synthetic materials, such as synthetic hydrogel polymers. Synthetic hydrogel polymers include, for example, carboxymethyl cellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, and polyvinyl pyrridines. Other suitable hydrogel polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water insoluble yet water swellable. Crosslinking may, for example, be by irradiation or covalent, ionic, van der Waals, or hydrogen bonding. Suitable superabsorbent materials are typically available from various commercial vendors, such as The Dow Chemical Company, Hoechst Celanese, Allied Colloids Limited, or Stockhausen, Inc. The hydrogel-forming polymeric material, employed in the absorbent articles of the present invention, suitably should be able to absorb a liquid under an applied load. For the purposes of this application, the ability of a hydrogel-forming polymeric material to absorb a liquid under an applied load, and thereby perform work, is quantified as the Absorbency Under Load (AUL) value. The AUL value is expressed as the amount (in grams) of an aqueous 0.9 weight percent sodium chloride solution which the hydrogel-forming polymeric material can absorb per gram of hydrogel-forming polymeric material under a load of about 0.3 pound per square inch (approximately 2.0 kilopascals) while restrained from swelling in the plane normal to the applied load. The hydrogel-forming polymeric material employed in the absorbent structures of the present invention suitably exhibit an AUL value of at least about 15, more suitably of at least about 20, and up to about 50. The method by which the AUL value may be determined is set forth, for example, in detail in US-A-5,149,335 or US-A-5,247,072, incorporated herein by reference.

Suitably, the hydrogel-forming polymeric material is in the form of particles which, in the unswollen state, have maximum cross-sectional diameters within the range of from about 50 microns to about 1000 microns, preferably within the range of from about 100 microns to about 800 microns, as determined by sieve analysis according to American Society for Testing and Materials (ASTM) test method D-1921. It is understood that the particles of hydrogel-forming polymeric material falling within the ranges described above may comprise solid particles, porous particles, or may be agglomerated particles comprising many smaller particles agglomerated into particles falling within the described size ranges.

The hydrogel-forming polymeric material is present in the absorbent composition of the present invention in an amount effective to result in the absorbent composition being able to absorb a desired amount of liquid. The hydrogel-forming polymeric material is beneficially present in the absorbent composition of the present invention in an amount of from about 80 to about 99 weight percent, suitably from about 85 to about 99 weight percent, and more suitably from about 85 to about 95 weight percent, based on total weight of the hydrogel-forming polymeric material and the magnetically-responsive material in the absorbent composition.

It has been discovered that, by combining the hydrogel-forming polymeric material with a magnetically-responsive material in an absorbent composition, it is possible to take advantage of the magnetic properties of the magnetically-responsive material in order to effectively and efficiently incorporate the absorbent composition into a disposable absorbent structure or product. By using a magnetically-responsive material in the absorbent composition, it is possible to use a magnetic field to selectively locate the absorbent composition within a disposable absorbent structure or product. It will be recognized, however, that it is generally desirable that the final disposable absorbent structure or product exhibits substantially no permanent magnetism under the conditions under which the final disposable absorbent structure or product will be used. It is desirable, therefore, that the magnetically-responsive material only be magnetically responsive when in a magnetic field yet remains substantially unmagnetized when a magnetic field is absent.

As such, as used herein, a "magnetically-responsive material" is generally meant to refer to a material selected from the group consisting of ferrimagnetic materials and superparamagnetic materials.

A ferrimagnetic material is a material in which the magnetic moments of neighboring domains tend to align antiparallel to each other, but the moments are of different magnitudes. This is in contrast, for example, to a ferromagnetic material wherein the magnetic moments of neighboring domains tend to align in a common direction. Examples of ferrimagnetic materials include maghemite (gamma $Fe_2O_3$), magnetite ($Fe_3O_4$), and ferrite. Ferrite is a compound having the chemical formula $XFe_2O_4$, wherein X represents a divalent metal, such as iron or zinc, whose size is such that it will fit into the crystal's structure. Ferrimagnetic materials may be commercially purchased for example, from Miles, Inc., Pittsburgh, PA, USA, or prepared in situ as described, for example, in US-A-5143583.

Suitably, the magnetically-responsive material such as a ferrimagnetic material has a coercivity of less than about 400 gauss (about 0.04 weber/square meter) and a remanence induction of less than about 2500 gauss (about 0.25 weber/square meter). Coercivity is the force required to demagnetize a material or, in other words, the amount of applied magnetic field that is required to overcome the magnetic induction of a material and bring its residual magnetism back to zero. Remanence is the residual magnetic flux density that remains in a material after the removal of an applied magnetic field. A superparamagnetic material is a material comprising fine particles in which the fine particles behave substantially independently of one another when a magnetic field is absent but, when placed in a magnetic field, are magnetized parallel to the magnetic field to an extent proportional to the magnetic field. An example of a superparamagnetic material is nanocrystal s of gamma $Fe_2O_3$.

Superparamagnetic materials may be purchased, for example, from Advanced Magnetics, Cambridge, MA, USA, or may be prepared in situ. Suitably, the superparamagnetic materials have a coercivity of about 0 gauss and a remanence induction of about 0 gauss.

The magnetically-responsive material is present in the absorbent composition of the present invention in an amount effective to result in the absorbent composition being magnetically responsive when in a magnetic field, yet the absorbent composition remains substantially unmagnetized when a magnetic field is absent. Beneficially, the magnetically-responsive material is present in the absorbent composition of the present invention in an amount of from about 1 to about 20 weight percent, more beneficially from about 1 to about 15 weight percent, and suitably from about 5 to about 15 weight percent, based on total weight of the hydrogel-forming polymeric material and the magnetically-responsive material in the absorbent composition. Typically, the lower limit of the amount of magnetically-responsive material that is to be used in the absorbent composition is determined by how well the magnetically-responsive material can be homogeneously mixed with the hydrogel-forming polymeric material. A more uniform dispersal of the magnetically-responsive material will typically result in less of the magnetically-responsive material being needed in order to achieve an effective and efficient incorporation of the absorbent composition into a disposable absorbent product as compared to where the magnetically-responsive material is not as uniformly dispersed within the absorbent composition. In addition, the upper and lower limits of the amount of magnetically-responsive material that is to be used in the absorbent composition may be affected by the nature of the magnetically-responsive material. As such, a lesser amount of a relatively stronger magnetically-responsive material will generally be needed as compared to a relatively weaker magnetically-responsive material. Generally speaking, one would like to use as little of the magnetically-responsive material as possible.

Many magnetically-responsive materials useful in the present invention have colors such as black, brown, or red. When the absorbent compositions of the present invention are used in a disposable absorbent structure or product, however, it will generally be desirable that the absorbent composition does not detract from the aesthetical appearance of the disposable absorbent structure or product. Thus, it will generally be desirable to use an absorbent composition that has a generally white or clear color. As such, it may be desirable to use a magnetically-responsive material that has a generally white or clear color. For example, one may use a transparent, gamma $Fe_2O_3$ material that has been developed by Xerox Corporation, as reported in the Chemical & Engineering News Journal of Jul. 20, 1992. Alternatively, an undesirably-colored, magnetically-responsive material or absorbent composition may be colored or coated so as to mask the undesirable color and exhibit a desired color. Suitably, a material used to mask the undesirable color does not substantially interfere with the absorbent or magnetic properties of the absorbent composition. For example, zinc oxide or cellulose acetate microfibers may be adhered to the undesirably colored material such as, for example, by using a fluidized bed process.

The hydrogel-forming polymeric material and the magnetically-responsive material may generally be mixed, or combined in any acceptable manner, in order to prepare the absorbent composition of the present invention, as long as the absorbent composition exhibits the desired absorbent and magnetic properties described herein. For example, the magnetically-responsive material may be added during the preparation or polymerization of the hydrogel-forming polymeric material such that the magnetically-responsive material becomes a chemical or physical part of, or becomes constrained or entrapped within, the structure of the hydrogel-forming polymeric material prepared. Alternatively, the magnetically-responsive material may be mixed with the already prepared hydrogel-forming polymeric material in, for example, an aqueous solution and then the absorbent composition is recovered from the solution. In such a preparation process, the hydrogel-forming polymeric material may swell or gel when in the aqueous solution so as to constrain or entrap the magnetically-responsive material within the swelled or gelled form of the hydrogel-forming polymeric material. Subsequent recovery of the absorbent composition as, for example, by evaporative drying will typically result in a substantially homogeneous mixture in which the magnetically-responsive material remains constrained or entrapped within the structure of the recovered form of the hydrogel-forming polymeric material. Another alternative method of mixing or combining the magnetically-responsive material and the hydrogel-forming polymeric material includes mixing both materials in combination with an adhesive material so that particles of the magnetically-responsive material become adhesively adhered to particles of the hydrogel-forming polymeric material. Other methods of mixing or combining the magnetically-responsive material and the hydrogel-forming polymeric material should be readily apparent to those skilled in the art.

The absorbent compositions according to the present invention are suited to absorb many liquids, such as water, saline, and synthetic urine, and body liquids such as urine, menses, and blood, and are suited for use in disposable absorbent products such as diapers, adult incontinent products, and bed pads; in catamenial devices such as sanitary napkins, and tampons; and in other absorbent products such as wipes, bibs, wound dressings, and surgical capes or drapes. Accordingly, in another aspect, the present invention relates to a disposable absorbent product comprising an absorbent composition as described herein.

Use of the described absorbent compositions in disposable absorbent products allows for the formation of a disposable absorbent product which is able to rapidly receive a discharged liquid and yet which product is thin. Typically, the absorbent composition will be incorporated into a disposable absorbent product in the form of an absorbent structure. Such disposable absorbent products generally comprise a liquid-permeable topsheet, a backsheet, and an absorbent structure, such as an absorbent structure comprising the absorbent composition of the present invention, located between the topsheet and backsheet.

Absorbent structures for incorporating an absorbent composition into a disposable absorbent product are generally well known. An absorbent structure may take the form, for example, of a batt of comminuted wood pulp fluff, a tissue layer, or of a web structure comprising an entangled fibrous mass formed, for example, from an extruded thermoplastic composition. Suitably, the absorbent structure is formed so as to constrain or entrap the absorbent composition within its structure. The absorbent composition may be incorporated into the absorbent structure either during or after the formation of the general form of the absorbent structure.

Exemplary disposable absorbent products are generally described in US-A-4,710,187; US-A-4,762,521; US-A-4,770,656; US-A-4,798,603; and U.S. Ser. No. 08/096,654, filed Jul. 22, 1993 in the name of Hansen et al., which references are incorporated herein by reference.

In one embodiment of the present invention, a disposable absorbent product is provided, which disposable absorbent product comprises topsheet, a backsheet, and an absorbent structure comprising a hydrogel-forming polymeric material and a magnetically-responsive material, wherein the absorbent structure is positioned between the topsheet and the backsheet.

While one embodiment of the invention will be described in terms of the use of an absorbent composition in an infant diaper, it is to be understood that the absorbent composition is equally suited for use in other disposable absorbent products known to those skilled in the art.

Turning now to the drawings, FIG. 1 illustrates a disposable diaper 1 according to one embodiment of the present invention. Disposable diaper 1 includes a backsheet 2, a topsheet 4, and an absorbent structure 6, located between the backsheet 2, and the topsheet 4. Absorbent structure 6 is an absorbent structure according to the present invention. Specifically, in the illustrated embodiment, absorbent structure 6 comprises an absorbent composition comprising a hydrogel-forming polymeric material and a magnetically-responsive material.

Those skilled in the art will recognize materials suitable for use as the topsheet and backsheet. Exemplary of materials suitable for use as the topsheet are liquid-permeable materials such as spunbonded polypropylene or polyethylene having a basis weight of from about 15 to about 25 grams per square meter. Exemplary of materials suitable for use as the backsheet are liquid-impervious materials, such as polyolefin films, as well as vapor-pervious materials, such as microporous polyolefin films.

Absorbent products and structures according to all aspects of the present invention are generally subjected, during use, to multiple insults of a body liquid. Accordingly, the absorbent products and structures are desirably capable of absorbing multiple insults of body liquids in quantities to which the absorbent products and structures will be exposed during use. The insults are generally separated from one another by a period of time.

Various methods may be used to incorporate an absorbent composition of the present invention into an absorbent structure or disposable absorbent product.

For example, the present invention can be employed to produce selected mixtures and distributions of an absorbent composition into a filamentary or fibrous material during an airlaying or airforming operation. The particular embodiment of the invention set forth in the following detailed description of the invention relates to distributing particles of an absorbent composition into a pad of cellulosic fluff. However, other mixtures of materials may be produced employing the present invention depending on the particular parameters desired in the absorbent structure. Such alternative configurations and uses are contemplated as being within the scope of the present invention.

Figure 2:
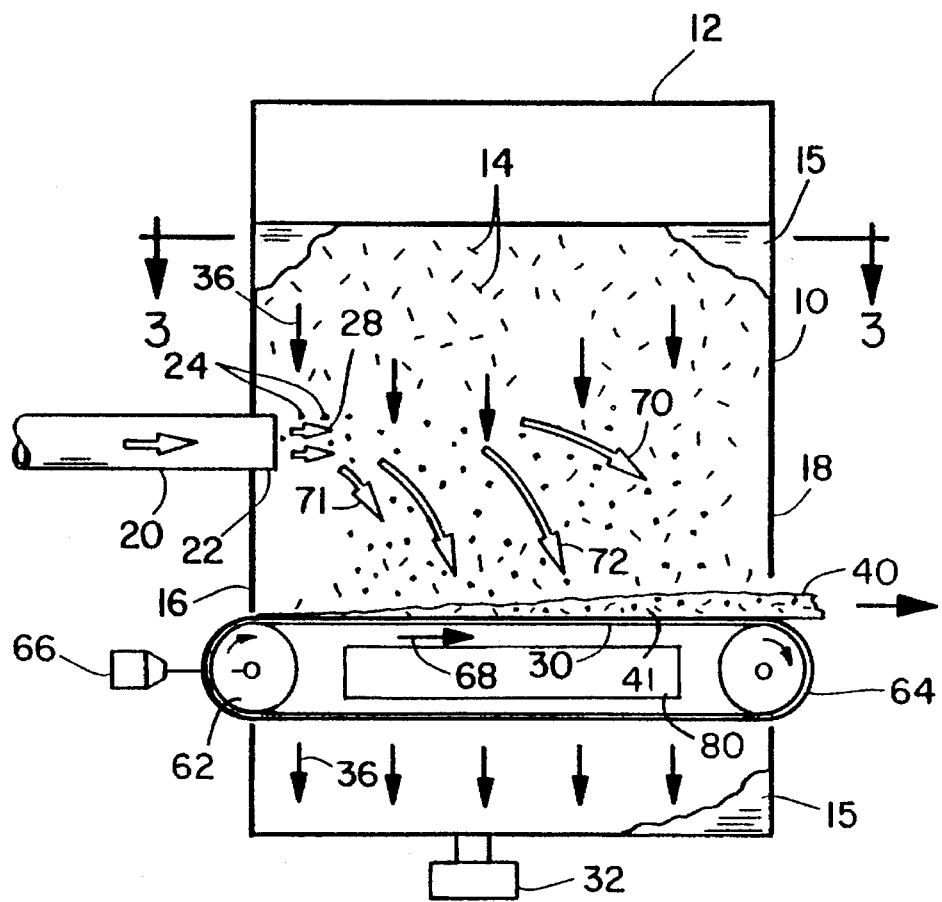
FIG. 2 illustrates a schematic view of a representative apparatus useful in the present invention.
Figure 3:
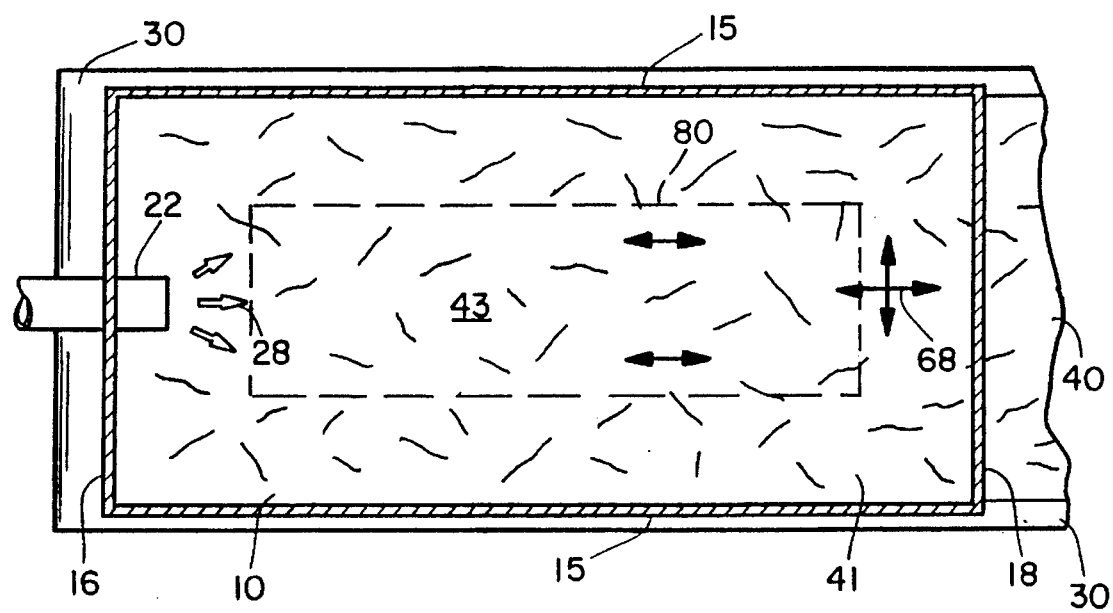
FIG. 3 illustrates a cross-sectional, top plan view of the forming chamber taken along line 3—3 of FIG. 2.

Referring now to FIGS. 2 and 3, a representative apparatus includes a forming chamber 10 and a fiber delivery means, such as fiberizer 12, for providing, a flow of fibrous material 14 within the forming chamber. A forming layer 30, which is located in forming chamber 10 and is moveable therein, receives a deposit of fibrous material 14 thereon. Conduit means, such as pipeline 20 and one or more nozzles 22, supply a flow of dispersed bodies of an absorbent composition 24. This flow of an absorbent composition enters forming chamber 10 and intermixes with the flow of fibrous material 14 therein. A regulating means may be used to control a flow velocity 28 of the absorbent composition 24 within the fibrous material 14 deposited onto forming layer 30 to form web 41. A magnetic-field generating means 80 is positioned beneath forming layer 30 to direct the positioning of the absorbent composition 24 within the fibrous material 14.

Forming chamber 10 includes sidewalls 15 and end walls which are constructed and arranged to define a generally enclosed volume. End walls 16 and 18 have suitable entrance and exit openings formed therethrough to allow the entry of forming layer 30 and the removal of airlaid absorbent structure 40 from the forming chamber.

Fiberizer 12 may comprise any one of a number of types of fiberizing devices, such as conventional hammermills. Sheets of selected fibrous material are typically fed into fiberizer 12, and are disintegrated into a plurality of individual fibers 14 which are ejected or otherwise introduced into chamber 10.

Fibers 14 are typically composed of absorbent, wood pulp fibers commonly referred to as fluff. The fibers may also be composed of staple fibers, polymeric fibers, cellulosic fibers and mixtures thereof, as well as mixtures of absorbent fibers with generally hydrophobic fibers.

The forming apparatus of the invention may further include vacuum means 32, such as a conventional blower mechanism, for creating a selected pressure differential through forming chamber 10 and past forming layer 30. The vacuum means is typically located underneath forming layer 30 to create an airflow through chamber 10 which is generally directed from fiberizer 12 and past forming layer 30.

This air flow helps to direct and control the deposit of fibers 14 and absorbent composition 24 onto the forming layer.

Forming layer 30, for example, comprises a forming screen configured as an endless belt which moves about support rollers 62 and 64. A suitable driving means, such as electric motor 66, is operably connected to move forming layer 30 through chamber 10 at a selected speed along movement direction 68. Fibers 14 and absorbent composition particles 24 deposit onto the portion of forming layer 30 within forming chamber 10 to form a web 41 which eventually develops into absorbent structure 40. Since web 41 moves generally from end wall 16 toward the exit opening through end wall 18, the depth or thickness of web 41 on any particular section of forming layer 30 gradually increases as that forming layer section traverses through the forming chamber. The fiber deposition rate onto forming layer 30, and the movement speed of the forming layer, can be suitably adjusted to control the finally formed thickness of the airlaid fibrous web 41. In addition, the positioning of and the strength of the magnetic field generated by magnetic-field generating means 80 may be adjusted to control or vary the positioning of the absorbent composition 24 within the airlaid fibrous web 41.

Figure 4:
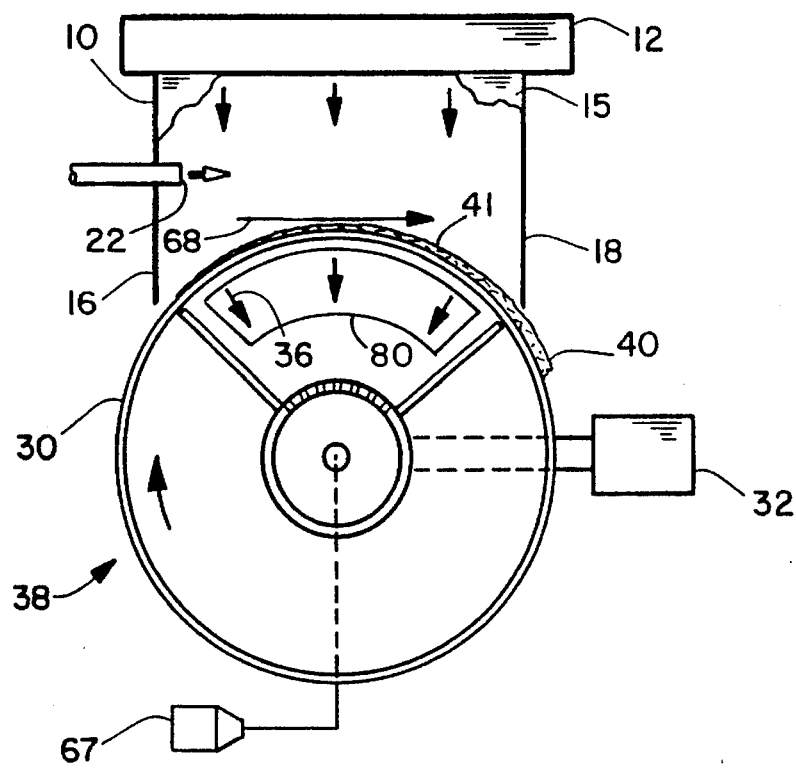
FIG. 4 illustrates an embodiment of a representative apparatus useful in the present invention which employs a drum former device.

In another aspect of the invention, forming layer 30 comprises a forming screen carrier on an outer circumferential surface of a rotatable drum 38, as representatively shown in FIG. 4. A suitable drive means, such as motor 67, rotatably activates drum 38 to move forming layer 30 through forming chamber 10.

The absorbent composition 24 may be supplied from a storage means (not shown). A desired flow rate of individual, particulate-type bodies of absorbent composition 24 may be supplied, for example, by a gaseous flow transport system means to a pipeline 20. Pipeline 20 then directs the absorbent composition 24 through nozzle 22 into forming chamber 10. The illustrated embodiment of the invention includes a single nozzle 22 which, for example, may comprise a conduit of circular cross-section. If desired, other regular or irregular nozzle shapes or sizes may be employed. The nozzle may protrude into chamber 10, if desired, to adjust the distribution of absorbent composition particles through the thickness of web 41. A larger amount of protrusion can reduce the amount of particles deposited near the forming layer side of web 41.

Figure 5:
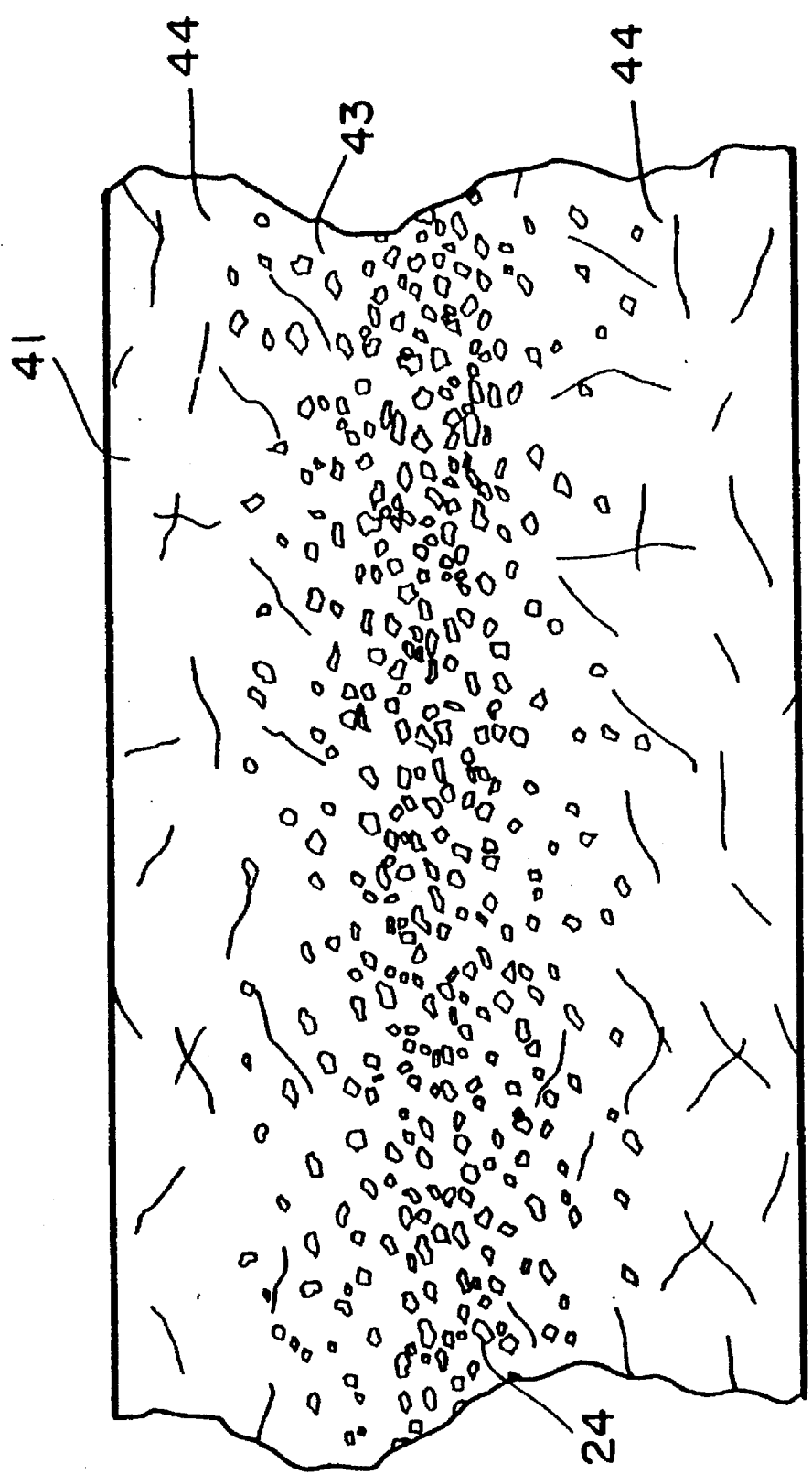
FIG. 5 representatively shows a cross-sectional, top view of an absorbent structure which includes a concentration gradient of absorbent composition along the cross-direction of the pad.

Depending on the size and weight of the individual particles of absorbent composition 24, the dispersed particles will tend to follow various trajectories 70–72 to intermix with the flow of fibers 14, moving through chamber 10 toward forming layer 30, to form an airlaid fibrous web 41 as represented in FIG. 5. Some of the particles will follow a shorter trajectory 71 to deposit absorbent composition 24 into web 41 at locations nearer end wall 16. Other particles will follow longer trajectories 70 to deposit into web 41 at locations closer to end wall 18. The remainder of particles will follow intermediate trajectories 72 to deposit into web 41 at more centrally located, intermediate regions between end walls 16 and 18. Since web 41 is gradually increasing in thickness as it traverses through chamber 10, particles 24 can be selectively distributed through the thickness dimension of web 41 to produce a desired concentration gradient therein. Suitably, absorbent composition particles 24 are selectively attracted to, and distributed over, a medial portion 43 of web 41, corresponding to the underlying location of the magnetic-field generating means 80. Conversely, the absorbent composition particles 24 are suitably not attracted to and, thus, not distributed over distal portions 44 of web 41.

Figure 6:
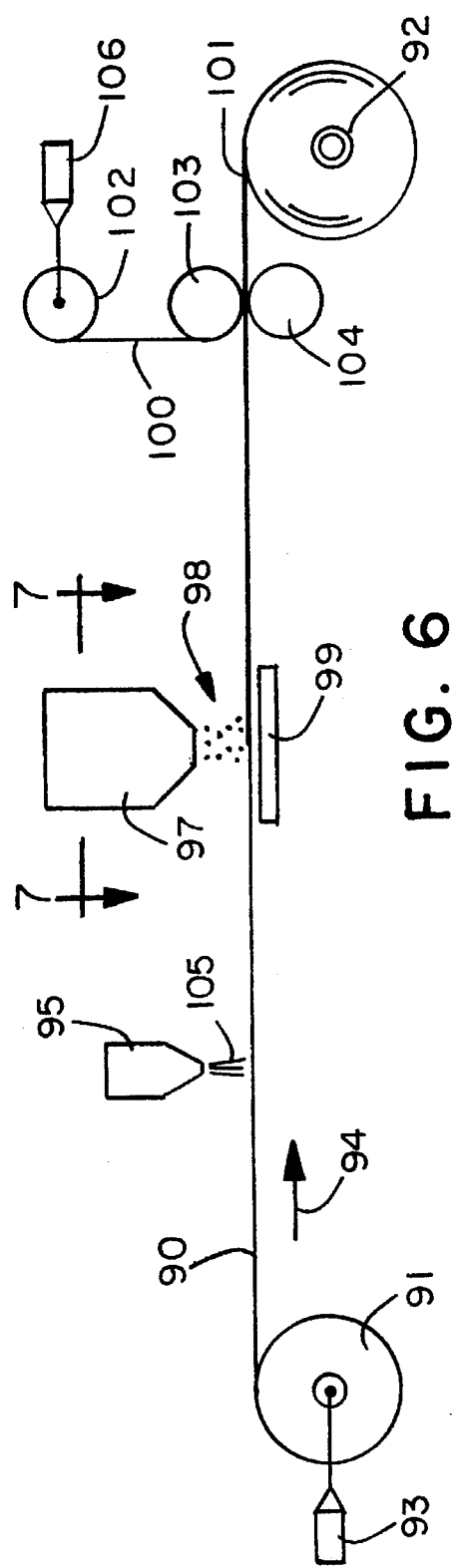
FIG. 6 illustrates a schematic view of a representative apparatus useful in the present invention.
Figure 7:
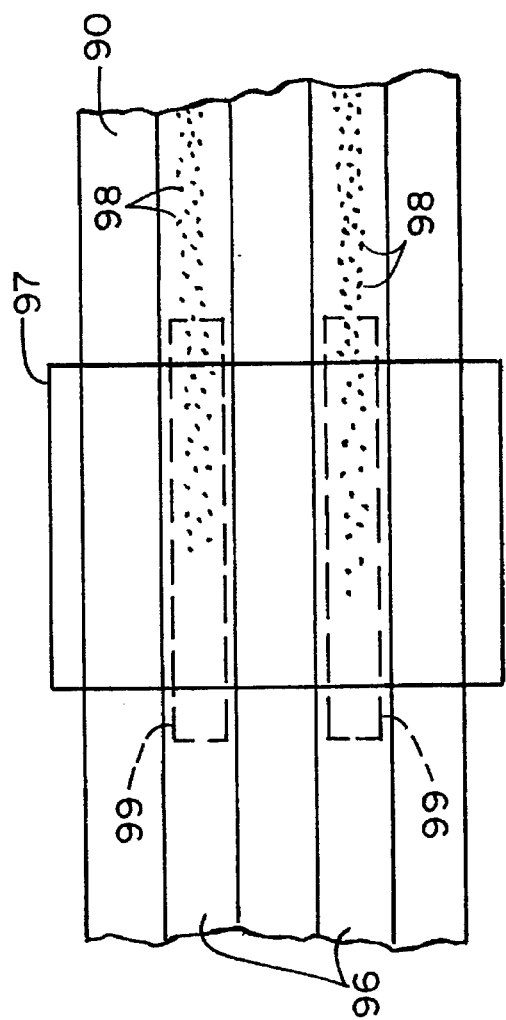
FIG. 7 illustrates a cross-sectional, top plan view of the adhesive composition delivery means taken along line 7—7 of FIG. 6.

Referring now to FIGS. 6 and 7 to describe another method for incorporating an absorbent composition into an absorbent structure, tissue support layer 90 travels from support roller 91 to collector roller 92. A suitable driving means, such as electric motor 93, is operably connected to move tissue support layer 90 at a selected speed along movement direction 94. As tissue support layer 90 travels underneath adhesive applicator means 95, adhesive 105 is gravimetrically applied to tissue support layer 90 to form adhesive lines 96. As tissue support layer 90 travels underneath absorbent composition delivery means 97, absorbent composition particles 98 are gravimetrically applied in the general location of the adhesive lines 96. A magnetic-field generating means 99 is located beneath tissue support layer 90, in the general location of absorbent composition delivery means 97, to direct the positioning of the absorbent composition particles 98 onto the adhesive lines 96. A tissue top layer 100 is then layered onto tissue support layer 90, thereby sandwiching the absorbent composition particles 98 between the tissue layers to form absorbent structure 101 which is collected on collector roller 92. Tissue top layer 100 travels from support roller 102 and is contacted with tissue support layer 90 between nip rollers 103 and 104. A suitable driving means, such as electric motor 106, is operably connected to move tissue top layer 100 at a selected speed from support roller 102 into contact with tissue support layer 90.

EXAMPLE 1

Thirty-six grams of a carboxymethyl cellulose (CMC) [commercially available from the Aqualon Company under the trade designation AQUALON® Cellulose Gum CMC-7H4F, having an average degree of substitution of about 0.7 and a viscosity in a 1 percent aqueous solution at 25° C. of about 2500–6000 centipoise] were blended into 2000 ml of water using a mixer. The blending is completed after about one hour. Four grams of iron oxide ($Fe_3O_4$) were then added to the mixture with additional blending for another two hours. The mixture was then dried in a convection oven at about 40° C. overnight and then in a convection oven at about 110° C. for about three hours. The final film was then ground with a high shear mixer and separated by sieves according to particle size. The particles were then cured in an oven at about 180° C. for about 20 minutes. The resulting absorbent composition is responsive to a magnetic field generated from a permanent magnet of about 1400 gauss but exhibits no magnetic properties when in the absence of a magnetic field.

EXAMPLE 2

To about 153.3 grams of water, under rapid stirring, was added about 0.375 mole of sodium hydroxide, about 0.5 mole of acrylic acid, a crosslinking agent, about 0.77 gram of methylene bis(acrylamide), and iron oxide ($Fe_3O_4$) in an amount of about 0.909 gram (about a 2 weight percent loading based on the weight of the hydrogel-forming polymeric material prepared). The vessel containing the added methylene bis(acrylamide) was then rinsed with about 10 milliliters of water. This water was then added to the reaction mixture to ensure a complete addition of all of the methylene bis(acrylamide) to the reaction mixture. The mixture was then swept with nitrogen for about 15 minutes, and the temperature of the mixture was brought to about 70° C. An initiator, potassium disulfur oxide ($K_2S_2O_8$) in an amount of about 0.2 gram dissolved in about 10 milliliters of water, was then added to the mixture. The mixture gels after completion of the reaction. After about another 60 minutes, the gel was cut up and dried at about 125° C. overnight.

The same procedure is followed except that iron oxide ($Fe_3O_4$) in an amount of about 0.4545 gram (about a 1 weight percent loading based on the weight of the hydrogel-forming polymeric material prepared) was added to the mixture.

Both of the resulting absorbent compositions are responsive to a magnetic field from a permanent magnet of about 1400 gauss but exhibit no magnetic properties when in the absence of a magnetic field.

EXAMPLE 3

Figure 8:
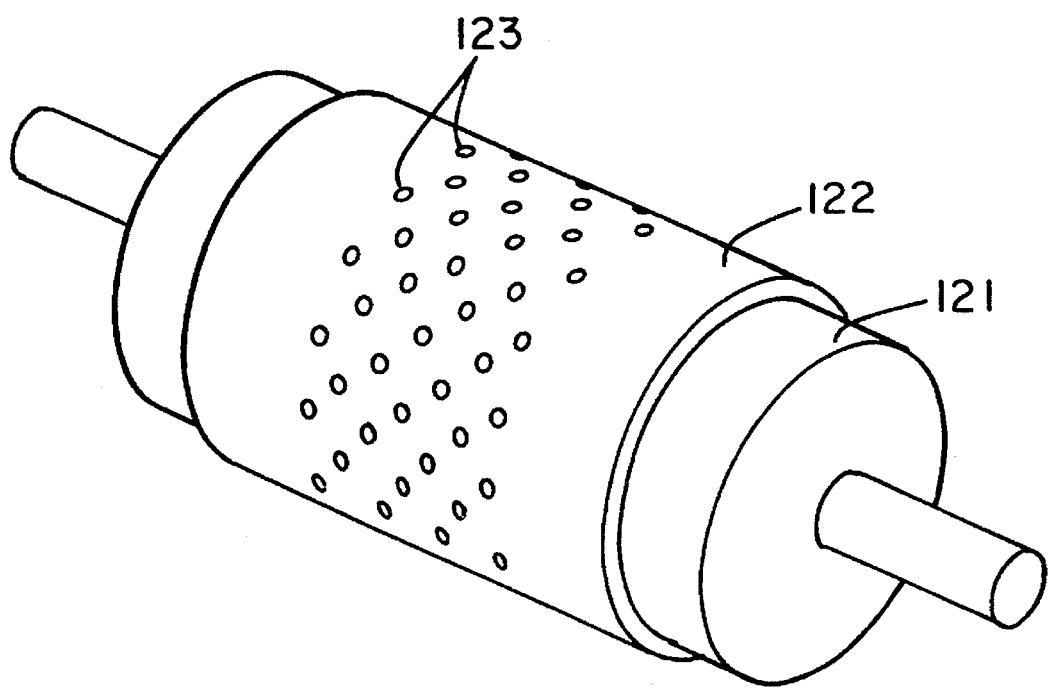
FIG. 8 illustrates a magnetic roll useful in the present invention.
Figure 9:
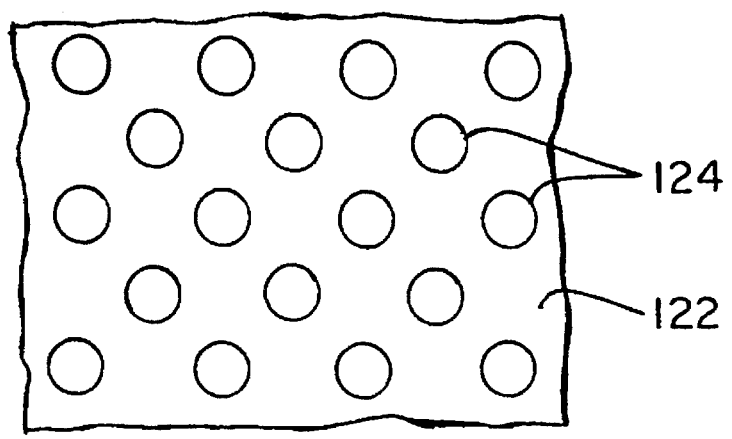
FIG. 9 illustrates a pattern for placing magnets in the magnetic roll as illustrated in FIG. 8.

Referring to FIGS. 8 and 9, a roll to magnetically place an absorbent composition was made from a 4 inch diameter steel roll 121 and a 4 inch diameter polyvinylchloride pipe 122. The polyvinylchloride pipe 122 was drilled to accept 0.375 inch diameter circular magnets 123 according to a pattern as shown in FIG. 9 and slid onto the steel roll 121. From center to center in a row or column, the magnets 123 were placed about 1.0134 inches apart, such that there were fourteen of the magnets 123 in a row around the circumference of the polyvinylchloride pipe 122. The magnets 123 were inserted into the drilled holes 124, such that all of the magnets 123 had the same polarity facing against the steel roll 121. The prepared magnet roll is used in a set-up similar to that shown in FIG. 10.

Figure 10:
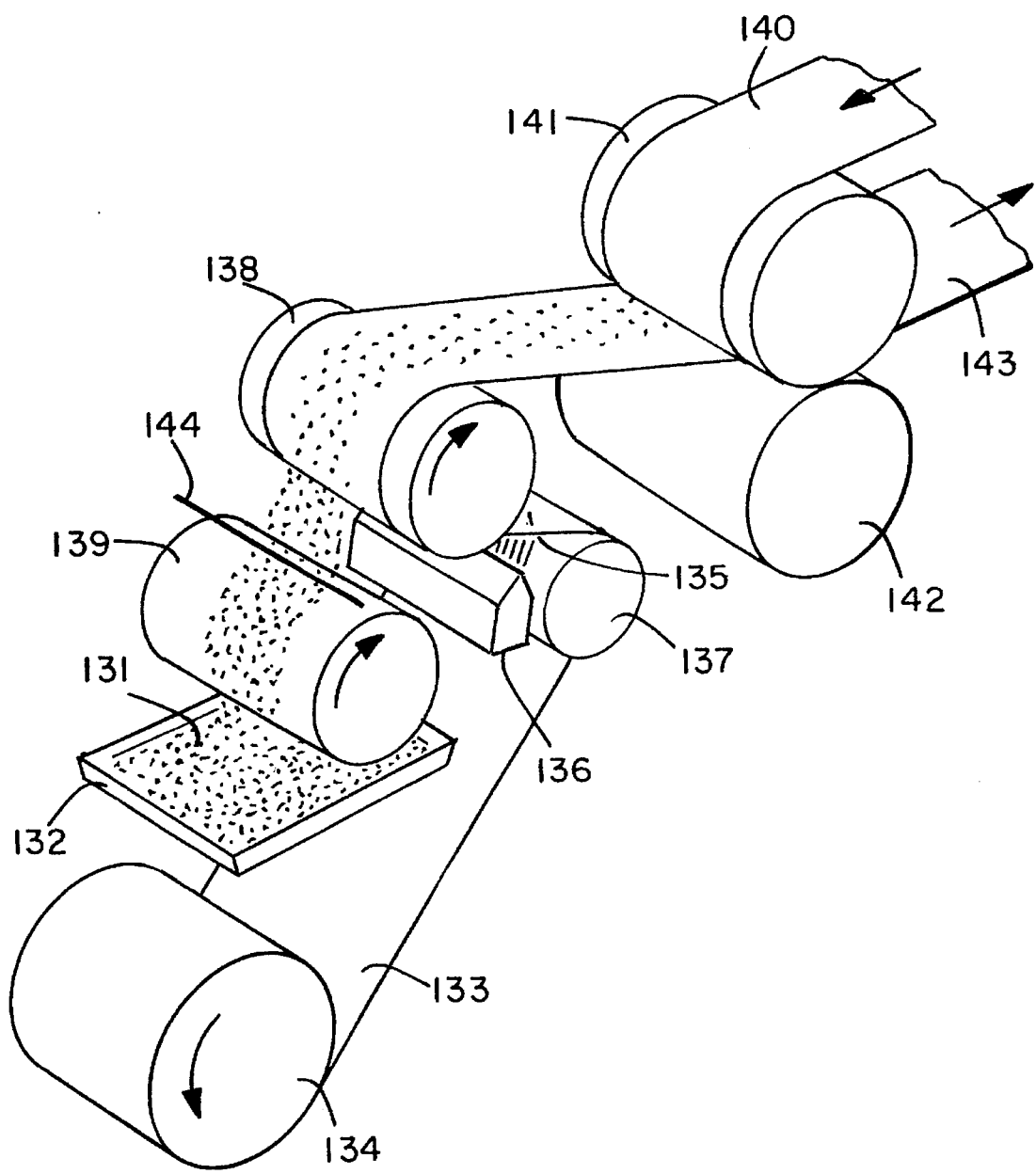
FIG. 10 illustrates a schematic view of a representative apparatus useful in the present invention.

Referring to FIG. 10, an absorbent composition 131 comprising microcrystalline cellulose and about 10 weight percent iron oxide ($Fe_3O_4$) is prepared by blending and is placed in an absorbent composition tray 132. A blue tissue substrate 133, having a cross section width of about 4 inches and a basis weight of about 0.5 ounce per square yard, is unwound from a substrate roll 134, passes over an idler roll 137, and is sprayed with a polyethylene oxide grafted polyvinylacetate hot-melt adhesive 135 from adhesive applicator 136. The blue tissue substrate 133 then passes over a magnetic roll 138, as shown in FIG. 8, which is grounded. The absorbent composition 131 is picked up from the absorbent composition tray 132 by a pickup roll 139. An electrostatic means such as a corona discharge wire 144, with an electric field of about $5 \times 10^5$ volts per meter, is used to transfer the absorbent composition 131 from the pickup roll 139 to the tissue substrate 133 wherein the absorbent composition 131 is attracted by the grounded magnetic roll 138. The corona discharge wire 144 electrically charges the air and, thus, the absorbent composition particles 131 on the pickup roll 139. The grounded magnetic roll 138 provides an opposite charge to that provided by the corona discharge wire 144, such that the absorbent composition particles 131 accelerate towards the magnetic roll 138. An adhesive-coated, hydroentangled pulp web 140, having a basis weight of about 1.75 ounces per square yard, is then layered onto the blue tissue substrate 133 and the combination passed through a set of nip rolls 141 and 142. The final product is an absorbent laminate structure 143. A sample of the final product was weighed to determine the amount of absorbent composition placed onto the blue tissue substrate. A 4-foot sample of the blue tissue substrate weighed about 8.21 grams and a 4-foot sample of the adhesive-sprayed hydroentangled pulp substrate weighed about 23.69 grams, such that a 4-foot sample of the combined substrate weighed about 31.90 grams.

Several 4-foot samples of the final absorbent laminate structure were prepared and weighed from about 43.65 to about 56.47 grams. As such, about 3 to about 6 grams of absorbent composition was placed per linear foot of substrate.

A similar procedure is run except that an otherwise identical absorbent composition, but without the magnetically-responsive material, is used. The amount of absorbent composition placed per linear foot of substrate was found to be about 1 gram. Thus, the use of an absorbent composition comprising a magnetically-responsive material results in from about 3 to about 6 times as much absorbent composition being placed into an absorbent laminate structure as compared to the use of an absorbent composition without the magnetically-responsive material.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

What is claimed is:

1. An absorbent composition comprising:

a hydrogel-forming polymeric material; and a magnetically-responsive material selected from the group consisting of ferrimagnetic materials and superparamagnetic materials wherein the magnetically-responsive material is present in the absorbent composition in an amount effective to result in the absorbent composition being magnetically responsive when in a magnetic field and wherein the absorbent composition remains substantially unmagnetized when a magnetic field is absent.

2. The absorbent composition of claim 1 wherein the hydrogel-forming polymeric material is able to absorb an amount of water at least about 10 times the weight of the hydrogel-forming polymeric material.

3. The absorbent composition of claim 1 wherein the hydrogel-forming polymeric material is selected from the group consisting of agar, pectin, and guar gum, carboxymethyl cellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, and polyvinyl pyrridines.

4. The absorbent composition of claim 1 wherein the hydrogel-forming polymeric material is selected from the group consisting of carboxymethyl cellulose and alkali metal salts of polyacrylic acid.

5. The absorbent composition of claim 1 wherein the absorbent composition comprises from about 80 to about 99 weight percent hydrogel-forming polymeric material and from about 1 to about 20 weight percent magnetically-responsive material, based on total weight of the hydrogel-forming polymeric material and the magnetically-responsive material in the absorbent composition.

6. The absorbent composition of claim 5 wherein the absorbent composition comprises from about 85 to about 99 weight percent hydrogel-forming polymeric material and from about 1 to about 15 weight percent magnetically-responsive material, based on total weight of the hydrogel-forming polymeric material and the magnetically-responsive material in the absorbent composition.

7. The absorbent composition of claim 6 wherein the absorbent composition comprises from about 85 to about 95 weight percent hydrogel-forming polymeric material and from about 5 to about 15 weight percent magnetically-responsive material, based on total weight of the hydrogel-forming polymeric material and the magnetically-responsive material in the absorbent composition.

8. The absorbent composition of claim 1 wherein the magnetically-responsive material is selected from the group consisting of maghemite, magnetite, ferrite, and nanocrystals of gamma $Fe_2O_3$.

9. The absorbent composition of claim 1 wherein the magnetically-responsive material has a coercivity of less than about 400 gauss and a remanence induction of less than about 2500 gauss.

10. A disposable absorbent product comprising a liquid-permeable topsheet, a backsheet, and an absorbent structure positioned between the topsheet and the backsheet, wherein the absorbent structure comprises an absorbent composition comprising a hydrogel-forming polymeric material and a magnetically-responsive material selected from the group consisting of ferrimagnetic materials and superparamagnetic materials, and wherein the magnetically-responsive material is present in the absorbent composition in an amount effective to result in the absorbent composition being magnetically responsive when in a magnetic field and wherein the absorbent composition remains substantially unmagnetized when a magnetic field is absent.

11. The disposable absorbent product of claim 10 wherein the hydrogel-forming polymeric material is able to absorb an amount of water at least about 10 times the weight of the hydrogel-forming polymeric material.

12. The disposable absorbent product of claim 10 wherein the hydrogel-forming polymeric material is selected from the group consisting of agar, pectin, and guar gum, carboxymethyl cellulose, alkali metal salts of polyacrylic acid, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, and polyvinyl pyrridines.

13. The disposable absorbent product of claim 10 wherein the hydrogel-forming polymeric material is selected from the group consisting of carboxymethyl cellulose and alkali metal salts of polyacrylic acid.

14. The disposable absorbent product of claim 10 wherein the absorbent composition comprises from about 80 to about 99 weight percent hydrogel-forming polymeric material and from about 1 to about 20 weight percent magnetically-responsive material, based on total weight of the hydrogel-forming polymeric material and the magnetically-responsive material in the absorbent composition.

15. The disposable absorbent product of claim 14 wherein the absorbent composition comprises from about 85 to about 99 weight percent hydrogel-forming polymeric material and from about 1 to about 15 weight percent magnetically-responsive material, based on total weight of the hydrogel-forming polymeric material and the magnetically-responsive material in the absorbent composition.

16. The disposable absorbent product of claim 15 wherein the absorbent composition comprises from about 85 to about 95 weight percent hydrogel-forming polymeric material and from about 5 to about 15 weight percent magnetically-responsive material, based on total weight of the hydrogel-forming polymeric material and the magnetically-responsive material in the absorbent composition.

17. The disposable absorbent product of claim 10 wherein the magnetically-responsive material is selected from the group consisting of maghemite, magnetite, ferrite, and nanocrystals of gamma $Fe_2O_3$.

18. The disposable absorbent product of claim 10 wherein the magnetically-responsive material has a coercivity of less than about 400 gauss and a remanence induction of less than about 2500 gauss.

* * * * *